(12) United States Patent
Engel et al.

(10) Patent No.: US 8,173,592 B1
(45) Date of Patent: *May 8, 2012

(54) METHOD FOR A PROGRAMMED CONTROLLED OVARIAN STIMULATION PROTOCOL

(75) Inventors: Jurgen Engel, Alzenau (DE); Hilde Riethmuller-Winzen, Frankfurt (DE)

(73) Assignee: Zentaris IVF GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/523,455

(22) Filed: Mar. 10, 2000

Related U.S. Application Data

(60) Provisional application No. 60/127,241, filed on Mar. 31, 1999, provisional application No. 60/131,632, filed on Apr. 28, 1999.

(51) Int. Cl.
*A61K 38/00* (2006.01)
*A61K 38/24* (2006.01)
*A61K 38/09* (2006.01)
*A61P 15/08* (2006.01)
*A61P 15/16* (2006.01)
*A61P 15/18* (2006.01)
*A61P 5/06* (2006.01)
*A61P 5/24* (2006.01)
*A61P 5/02* (2006.01)
*C07K 14/59* (2006.01)

(52) U.S. Cl. ........ 514/9.8; 514/9.9; 514/10.1; 514/10.2; 514/10.3; 514/10.5; 514/10.6; 514/841

(58) Field of Classification Search .................... 514/15, 514/12, 841, 800, 171, 9.8–10.6
See application file for complete search history.

(56) References Cited

U.S. PATENT DOCUMENTS

| 4,016,259 A | * | 4/1977 | Kent ............................. 424/177 |
| 5,470,847 A | * | 11/1995 | Garfield ........................ 514/565 |
| 5,945,128 A | * | 8/1999 | Deghenghi .................... 424/501 |

FOREIGN PATENT DOCUMENTS

| CA | 2200541 | 7/1998 |
| EP | 0 788 799 | 8/1997 |
| WO | HU 221589 | 9/1990 |
| WO | HU 218910 | 2/1996 |

OTHER PUBLICATIONS

Rabasseda X.; Leeson P.; Castaner J., Drugs of the Future, (1999) 24/4 (393-403).*
Hardman et al. "Goodman & Gilman's The Pharmacological Basis of Therapeutics" (9th ed, 1996) p. 51 and 57-58.*
Hall et al, Variable Tolerance of the Developing Follicle and Corpus Luteum to Gonadotropin-Releasing Hormone Antagonist-Induced Gonadotropin Withdrawal in the Human, 1991, Journal of Clinical Endocrinology and Metabolism, 72(5), pp. 993-1000.*
Ziegler et al, Synchronization of Endogenous and Exogenous FSH Stimuli in Controlled Ovarian Hyperstimulation (COH), 1998, Human Reproduction, 13(3), pp. 561-564.*
Olivennes et al, The Single or Dual Administration of the Gonadotropin-releasing Hormone Antagonist Cetrorelix in an In Vitro Fertilization-Embryo Transfer Program, 1994, Fertility and Sterility, 62(3), pp. 468-476.*
Gonen et al, Gonadotropin Suppression with Oral Contraceptives Before In Vitro Fertilization, 1990, Fertility and Sterility, 53(2), pp. 282-287.*
International search report of corresponding PCT application PCT/EP00/02466 dated Aug. 23, 2000.
Foreign search report dated Mar. 5, 2004 issued by Hungarian Patent Office.
Chun et al., "Hormonal Regullatin of apoptosis in early antral follicles: follicle-stimulating hormone as a major survival factor," Endocrinology, 137 ed., Abstract, vol. 137 ( No. 4), p. 1447-56, (Apr. 1996).
E.R. Hernandez, "Embryo implantation and GnRH antagonists: embryo implantation: the Rubicon for GnRH antagonists," Hum. Reprod. , Abstract, vol. 15 ( No. 6), p. 1211-6, (Jun. 2000).
DeLaFuente et al., "Epidermal growth factor enhances preimplantation developmental competence of maturing mouse oocytes," Human Reproduction, vol. 14 ( No. 12), p. 3060-3068, (1999).
C. Albano et al., "Hormonal profile during the follicular phase in cycles stimulated with a combination of human menopausal gonadotrophin and gonadotrophin-releasing hormone antagonist (Cetrorelix)", Human Reproduction, vol. 11, No. 10, pp. 2114-2118, 1996 XP-0020075394.
P. Bouchard et al., "Endocrine features of combined gonadotropin and GnRH antagonist ovulation induction", From Broker Team, pp. 115-119, XP-002111491, Ovulation Induction Update '98 (1998).
R. Felberbaum et al., 'Multiple dose protocol for the administration of GnRH-antagonists in IVF: the "Lübeck-protocol"', 10th World Congress on In Virto Fertilization and Assisted Reproduction, May 1997, pp. 397-404, XP-000933573.

* cited by examiner

*Primary Examiner* — Sreeni Padmanabhan
*Assistant Examiner* — Kendra D Carter
(74) *Attorney, Agent, or Firm* — Pillsbury Winthrop Shaw Pittman LLP

(57) ABSTRACT

A method of therapeutic management of infertility by programming of controlled ovarian stimulation and assisted reproductive procedures is disclosed containing the steps of a) suppression of premature ovulation with an LHRH-antagonist in controlled ovarian stimulation and assisted reproductive techniques with multiple follicle and oocyte development; b) programming the start of controlled ovarian stimulation by the administration to a patient of progestogen only-preparations or, alternatively, combined oral contraceptive preparations; c) exogenous stimulation of the ovarian follicle growth; d) ovulation induction with HCG, native LHRH, LHRH-agonists or recombinant LH; and e) application of assisted reproduction techniques, especially of IVF, ICSI, GIFT, ZIFT or by intrauterine insemination by sperm injection, wherein onset of the patient's menstrual cycle and of controlled ovarian stimulation are programmed in order to perform oocyte pickup and fertilization procedures during Mondays to Fridays.

19 Claims, No Drawings

METHOD FOR A PROGRAMMED CONTROLLED OVARIAN STIMULATION PROTOCOL

This is application claims priority from U.S. Provisional Application No. 60/127,241, filed Mar. 31, 1999, and from U.S. Provisional Application No. 60/131,632, filed Apr. 28, 1999, each of which is incorporated herein in its entirety.

FIELD OF INVENTION

Women are fertile for a limited time only. Unwanted childlessness occurs in one of 10 couples. The reason for unfulfilled wish for children is related to female factors, e.g. blocked or missing tubes, polycystic ovary disease, or to male factors, e.g. insufficient sperm motility.

To overcome this problem, female partners of infertile couples undergo ovarian stimulation with gonadotropins like HMG (human menopausal gonadotropin), FSH (follicle stimulating hormone) or by the antioestrogen clomiphene and gonadotropins.

This therapy stimulates the growth of a cohort of 6-12 follicles and oocytes to guarantee the fertilisation of sufficient oocytes by highly specified laboratory technologies. During this procedure a premature ovulation indicated by an LH and progesterone surge is prevented by the administration of LHRH-analogues, either by LHRH-antagonists or by LHRH-agonists.

BACKGROUND INFORMATION AND PRIOR ART

According to the known treatment protocols HMG is given on day 2 of the menstruation cycle. A single or multiple dose of 0.25 mg to 5 mg of LHRH antagonist Cetrorelix was administered to prevent LH surges on day 5 until and including the day of ovulation induction with HCG. (Hum. Reprod. 1994 May; 9(5):788-91, Hum. Reprod. 1995 June; 10(6): 1382-6, Fertil. Steril. 1997; 67:917-22, Hum. Reprod. 1998 September; 13(9)2411-4)

In the PCT application WO 98/58657 the LHRH antagonist ganirelix in an amount of 0.125-1 mg is administered in the method to prevent premature LH surges in women undergoing controlled ovarian hyperstimulation in combination with exogeneous FSH.

The EP 161 063 also teaches the use of a gonadotropin releasing hormone antagonist to prepare a pharmaceutical composition comprising a gonadotropin selected from HMG and FSH in the treatment of female infertility to suppress estrogen variability, in which treatment the antagonist composition is administered in an effective amount cojointly with the gonadotropin composition.

Usually for controlled induction of ovulation and final follicle maturation HCG (human chorionic gonadotropin) is given. 36 hours thereafter oocytes are picked up (OPU) by transvaginal or laparoscopic follicle puncture.

For the fertilisation of multiple oocytes by the sperms of the male partner assisted reproductive techniques (ART) are applied like IVF (in-vitro-fertilisation), ICSI (intracytoplasmic sperm injection), GIFT (gamete intra-Fallopian transfer) or ZIFT (zygote intra-Fallopian transfer) in highly specialized laboratories on the day of OPU.

Normally, two to four days after extracorporeal fertilization embryo transfer is performed by the replacement of several embryos into the cavum uteri to obtain pregnancy.

As many follicles develop following controlled ovarian stimulation therapy (COS) ovarian enlargement occurs and many oocytes are picked up. Therefore, oocyte pick up procedures have to be done in the operating theatre and with the application of general or regional anesthesia.

Assisted reproductive techniques are carried out in highly specialized laboratories by qualified personnel thereafter.

Preferably, these procedures have to be included into the routine operating theatre plans from Mondays to Fridays. The performance of oocyte pick up as well as of embryo transfer on weekends or holidays is avoided due to lack of enough qualified personnel on duty in most clinics. Furthermore, some hospitals undertake these procedures only on a few days each month in order to have the oocyte pick up and fertilization procedures performed by a highly specialized service team to increase the number of oocytes obtained as well as the fertilization rates and the number of good quality embryos. Therefore, programmed ovarian stimulation protocols are applied.

OBJECT OF THE INVENTION

The present invention especially relates to the improvement of the method of programming of ovarian stimulation procedures, i.e. the administration of LHRH-antagonists in controlled ovarian stimulation where the start of menstrual cycle and ovarian stimulation was programmed.

SUMMARY OF THE INVENTION

In a controlled ovarian stimulation procedure conducted with an LHRH-antagonist for the prevention of premature ovulation, gonadotropin injection is started at cycle day one to three of a menstrual cycle and is continued until the day of HCG when enough big follicles have developed.

The LHRH-antagonist is given at the days of risk of premature ovulation. The duration of ovarian stimulation takes normally ten days in these treatment cycles.

In order to perform oocyte pick up and fertilization procedures during Mondays to Fridays the start of a menstrual cycle and of COS are programmed.

For the programming of the start of the menstrual cycle and of controlled ovarian stimulation procedures oral contraceptives or progestogen-only containing preparations are given in the follicular phase, preferably starting at menstrual cycle day 1 or 2, or in the late luteal phase of the previous menstrual cycle.

The LHRH antagonist Cetrorelix was also used successfully for this purpose previously when 1 mg were given in the luteal phase and luteal regression was obtained and menses started 2 to 4 days later.

The duration of oral contraceptive or progestogen administration will be a minimum of ten up to a maximum of 25 days. Intake of the last tablet will preferably be on a Monday to Thursday to obtain start of menstrual bleeding and of ovarian stimulation therapy on Fridays to Mondays. Thereafter, oocyte pick up and further ART procedures can be scheduled and undertaken on Mondays to Thursdays.

The in a controlled ovarian stimulation procedure applied LHRH-antagonist for the prevention of premature ovulation can be for instance cetrorelix, teverelix, ganirelix antide or abarelix.

It is further in scope of the invention that the programming of COS and ART procedures is performed by oral administration of progestogen preparations, ethinylestradiol and progestogen, combined mono- bi- and triphasic contraceptive preparations containing contraceptive preparations, mestranol and progestogen, as well as by subcutaneous injection of LHRH antagonists.

The LHRH antagonists may be cetrorelix, teverelix, ganirelix, antide or abarelix and should be administered during the luteal phase in a dosage of 0.5 mg to 10 mg. The ovarian stimulation is performed by administration of urinary or recombinant FSH or HMG, with or without recombinant LH and with antioestrogens as for example clomiphene also with a combination of antioestrogens as for example clomiphene with gonadotropins.

EXAMPLE

Material and Methods

A total of 30 patients, 15 from each German study center was enrolled for one treatment cycle. In the pre-treatment cycle, each patient received monophasic oral contraceptive (OC) pills containing 30 μg Estradiol in combination with levonogastrel. Gonal-F® administration starting at dose 150 IU or 225 IU began on the first day of withdrawal bleeding after OC treatment. Cetrotide® 0.25 mg was given daily from the evening of stimulation day (s-day) 5/morning of s-day 6 until the day before hCG administration. On the basis of the ultrasound scans performed on s-day 9/10(s-day 9/10), and a calculation of follicular growth of 2 mm per day, hCG was administered to trigger ovulation (when >2 follicle's≧18 mm) were visualized.

Efficacy endpoint assessed included number of follicles ≧18 mm on s-day 9/10, total number of vials of Cetrotide® and ampoules of Gonal-F® used, duration of Cetrotide® and Gonal-F® treatments, number of patients receiving hCG, patients undergoing oocyte retrieval, number of oocytes retrieved, reliability of prediction of day of oocyte retrieval, and pregnancy rate. Safety end-points were indicated and severity of adverse events.

Results

Preliminary results from 17 patents show that the mean number of follicles ≧18 mm on s-day 9/10 was 2.2. On the last day of Cetrotide® administration the mean number of follicles with diameters of ≦14 mm, 15-17 mm and ≧18 mm were 2.7, 4.9 and 2.7 respectively. A median number of 24 ampoules of Gonal-F® equivalent to 75 IU were administered for 10.0 days, and daily injections of Cetrotide® 0.25 mg were administered for 5.7 days on average, respectively. All 17 women who received hCG had ovum pick up and embryo transfer. Overall, a mean number of 8.8 oocytes were retrieved and a mean of 2 embryos was transferred.

The pregnancy rate per attempt/cycle was 41%. The difference between predicted and actual day of OPU was 2 day on average. There as no cases of OHSS nor adverse events.

CONCLUSIONS

This is the first result of the use of Cetrotide® in COS cycles programmed by OCs. Overall, the stimulation results are similar to those observed in non-programmed cycles. Cetrotide® appears to be effective in OC programmed cycles, is well tolerated and allows reliable prediction of the day of oocyte retrieval. Thus use of Cetrotide® in programmed stimulation cycles represents another step towards well-tolerated, effective and convenient procedures in ART.

Cetrotide® is the registered Trade Mark for the LHRH Antagonist cetrorelix.

The various embodiments which have been described herein intended to be representative and not limiting, as various changes and modifications can be made in the present invention without departing from the spirit and scope thereof.

The invention claimed is:

1. A method of programming an infertility treatment cycle comprising controlled ovarian stimulation (COS) and assisted reproductive techniques (ART), the method comprising:

determining a luteal phase of a first menstrual cycle in an infertile patient;

administering a first dose regimen of an LHRH antagonist during said luteal phase of said first menstrual cycle, wherein said first dose regimen of LHRH antagonist induces a luteal regression;

terminating said first dose regimen administration prior to the onset of menses;

determining a follicular phase of a second menstrual cycle wherein said second menstrual cycle immediately succeeds said first menstrual cycle;

administering a follicle stimulating compound during said follicular phase, wherein said follicle stimulating compound stimulates ovarian follicle growth;

administering a second dose regimen of said LHRH antagonist during said follicular phase, wherein said second dose regimen of an LHRH antagonist suppresses premature ovulation;

administering HCG thereby inducing ovulation; and applying assisted reproduction techniques.

2. A method of programming an infertility treatment cycle according to claim 1, wherein said LHRH antagonist is selected from the group consisting of cetrorelix, teverelix, ganirelix, antide, and abarelix.

3. A method of programming an infertility treatment cycle according to claim 1, wherein said follicle stimulating compound is selected from the group consisting of urinary FSH, recombinant FSH, HMG, recombinant LH, clomiphene, or a combination thereof.

4. The method of claim 1, wherein said assisted reproduction techniques are carried out during routine operations of laboratories, clinics, hospitals or other assisted reproduction facilities.

5. The method of claim 1, wherein said second dose administers cetrorelix.

6. The method of claim 1, wherein said second dose administers teverelix.

7. The method of claim 1, wherein said second dose administers ganirelix.

8. The method of claim 1, wherein said second dose administers antide.

9. The method of claim 1, wherein said second dose administers abarelix.

10. The method of claim 1, wherein said first dose administers cetrorelix.

11. The method of claim 1, wherein said first dose administers teverelix.

12. The method of claim 1, wherein said first dose administers ganirelix.

13. The method of claim 1, wherein said first dose administers antide.

14. The method of claim 1, wherein said first dose administers abarelix.

15. The method of claim 3, wherein said follicle stimulating compound is selected from the group consisting of urinary FSH, recombinant FSH, HMG, recombinant LH, or a combination thereof.

16. The method of claim 3, wherein said follicle stimulating compound is clomiphene.

17. The method of claim 1, wherein said ovarian stimulation is achieved by administration of antioestrogens and gonadotropins.

18. The method of claim 1, wherein said ovarian stimulation is achieved by administration of clomiphene and gonadotropins.

19. The method of claim 1, wherein said assisted reproduction techniques comprise applying IVF, ICSI, GIFT, ZIFT or intrauterine insemination via sperm injection.

* * * * *